(12) United States Patent
Sugimoto et al.

(10) Patent No.: US 7,927,623 B2
(45) Date of Patent: Apr. 19, 2011

(54) TABLETS QUICKLY DISINTEGRATED IN ORAL CAVITY

(75) Inventors: Masaaki Sugimoto, Itami (JP); Hideki Murakami, Kobe (JP); Yoshiyuki Koida, Katano (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 1246 days.

(21) Appl. No.: 10/468,208

(22) PCT Filed: Feb. 12, 2002

(86) PCT No.: PCT/JP02/01140
§ 371 (c)(1),
(2), (4) Date: Aug. 18, 2003

(87) PCT Pub. No.: WO02/064119
PCT Pub. Date: Aug. 22, 2002

(65) Prior Publication Data
US 2004/0109890 A1 Jun. 10, 2004

(30) Foreign Application Priority Data
Feb. 15, 2001 (JP) .................. 2001-038343

(51) Int. Cl.
*A61K 31/33* (2006.01)
*A61K 31/555* (2006.01)
*A61K 31/50* (2006.01)
*A61K 31/535* (2006.01)
*A61K 31/497* (2006.01)
*A61K 31/03* (2006.01)
*A61K 31/025* (2006.01)
*A61K 9/20* (2006.01)
*A61K 9/36* (2006.01)
*A01N 43/00* (2006.01)
*A01N 55/02* (2006.01)
*A01N 43/58* (2006.01)
*A01N 29/04* (2006.01)
*A01N 29/02* (2006.01)

(52) U.S. Cl. ........ 424/464; 424/480; 514/183; 514/185; 514/228.8; 514/252.12; 514/252.13; 514/252.14; 514/751; 514/758

(58) Field of Classification Search .................. None
See application file for complete search history.

(56) References Cited

U.S. PATENT DOCUMENTS

| | | | |
|---|---|---|---|
| 5,011,694 A * | 4/1991 | Nuernberg et al. ........... 424/464 |
| 5,073,048 A | 12/1991 | Adachi et al. | |
| 5,254,355 A * | 10/1993 | Smith et al. ................. 426/285 |
| 5,501,861 A * | 3/1996 | Makino et al. ................. 424/464 |
| 5,861,396 A | 1/1999 | Niewohner et al. | |
| 5,861,404 A | 1/1999 | Niewohner et al. | |
| 5,866,571 A | 2/1999 | Niewohner et al. | |
| 5,902,824 A | 5/1999 | Ulrich et al. | |
| 5,981,527 A | 11/1999 | Daugan et al. | |
| 6,001,847 A | 12/1999 | Daugan et al. | |
| 6,037,346 A * | 3/2000 | Doherty et al. ........... 514/252.03 |
| 6,069,156 A | 5/2000 | Oku et al. | |
| 6,080,782 A | 6/2000 | Ulrich et al. | |
| 6,087,311 A * | 7/2000 | Van Dijk ........................ 510/294 |
| 6,127,378 A | 10/2000 | Gutterer | |
| 6,140,329 A | 10/2000 | Daugan | |
| 6,149,938 A | 11/2000 | Bonadeo et al. | |
| 6,191,138 B1 | 2/2001 | Gutterer | |
| 6,656,935 B2 * | 12/2003 | Yamada et al. ............. 514/230.5 |
| 2003/0032647 A1 * | 2/2003 | Yamada et al. ........... 514/255.05 |

FOREIGN PATENT DOCUMENTS

| | | |
|---|---|---|
| CA | 2 383 466 A1 | 3/2001 |
| EP | 0 995 750 A1 | 4/2000 |
| EP | 0 995 751 A2 | 4/2000 |
| EP | 1 219 609 A1 | 7/2002 |
| JP | 41-1273 B | 2/1966 |
| JP | 48-20103 B | 6/1973 |
| JP | 08-019589 A | 1/1996 |
| JP | 8-143473 A | 6/1996 |
| JP | 08-253457 A | 10/1996 |
| JP | 9-48726 A | 2/1997 |
| JP | 10-298061 A | 10/1998 |
| JP | 10-298062 A | 11/1998 |
| JP | 11-12161 A | 1/1999 |
| JP | 2000-072675 A | 3/2000 |
| JP | 2000-072751 A | 3/2000 |
| JP | 2000-095759 A | 4/2000 |
| WO | 94/28902 A1 | 12/1994 |
| WO | 96/16657 A1 | 6/1996 |
| WO | 98/38168 A1 | 9/1998 |
| WO | WO-98/53798 A1 | 12/1998 |
| WO | WO 98/53798 A1 | 12/1998 |
| WO | WO 99/59544 A2 | 11/1999 |
| WO | WO 00/06126 A1 | 2/2000 |
| WO | WO-00/06126 A1 | 2/2000 |
| WO | WO 00/24379 A1 | 5/2000 |
| WO | WO 00/24383 A1 | 5/2000 |
| WO | WO-00/57857 A1 | 10/2000 |
| WO | WO 01/19802 A1 | 3/2001 |
| WO | WO-01/19802 A1 | 3/2001 |

* cited by examiner

OTHER PUBLICATIONS

Ansel (Pharmaceutical Dosage forms and drug delivery systems 7th Ed, 1999; Lippincott Williams & Wilkins, NY pp. 89-91, 203 and 209).*
English Abstract of JP-09048726, Feb. 18, 1997.

*Primary Examiner* — Ernst V Arnold
(74) *Attorney, Agent, or Firm* — Birch, Stewart, Kolasch & Birch, LLP (57) ABSTRACT

Intraorally rapidly disintegrating tablets which, when ingested, disintegrates in the oral cavity rapidly without presenting unpleasant taste, can be quickly absorbed in the digestive tract and express efficacy are provided. The intraorally rapidly disintegrating tablets contain a drug being hardly water-soluble under neutral or alkaline conditions and being highly water-soluble under acidic conditions yet presenting unpleasant taste, which tablets can be prepared by combining the medicinal substance with a water-soluble acidic substance, coating either or both of the substances with a water-soluble coating agent being insoluble in alcoholic solvent, further adding a water-soluble binding agent being soluble in alcoholic solvent and a water-soluble saccharide, subjecting the resultant mixture to compression, and treating the products with an alcoholic solvent.

12 Claims, 3 Drawing Sheets

TABLETS QUICKLY DISINTEGRATED IN ORAL CAVITY

This application is the national phase under 35 U.S.C. §371 of PCT International Application No. PCT/JP02/01140 which has an International filing date of Feb. 12, 2002, which designated the United States of America.

TECHNICAL FIELD

The present invention relates to tablet preparations which rapidly/quickly disintegrate in the oral cavity. More specifically, the present invention relates to a preparation of an intraorally rapidly disintegrating tablet containing a medicinal substance (drug) being hardly water-soluble under neutral or alkaline conditions and being highly water-soluble under acidic conditions yet presenting unpleasant taste, which preparation comprises a water-soluble acidic substance and in which at least one of the medicinal and the acidic substances is coated with a water-soluble coating agent being insoluble in alcoholic solvent and whereby said preparation expresses efficacy rapidly after ingestion without presenting unpleasant taste owing to the drug in the process of disintegration in the oral cavity.

BACKGROUND ART

In general, basic drugs show low water-solubility as a compound in the free form per se under neutral or alkaline conditions. Accordingly, when a person who just finished eating or is suffering from anacidity takes such a drug, troubles including the delay of onset of efficacy and/or reduction of bioavailability (BA), etc. may be brought about because the drug ingested does not dissolve well.

In such cases, for the time being, drugs having a low solubility in water under neutral or alkaline conditions are converted into acid addition salts for the purpose of achieving rapid dissolution, improved bioavailability and early onset of efficacy thereof.

Besides, tablets or granules which quickly/rapidly disintegrate in the oral cavity have become available in these days so as to achieve early onset of action and easy ingestion. However, in these preparations, a drug begins to dissolve even in the oral cavity, and, therefore, even though said drug in the form of acid addition salt is highly water soluble, such preparations per se can hardly be administered to a patient as an intraorally rapidly disintegrating tablet or granule, if said drug has unpleasant taste.

There has been proposed a taste-masking technique, which, for example, comprising previously coated granules comprising acid addition salts of a drug with a polymer being soluble at low pH. For example, WO98/30209 discloses granulated preparation of sildenafil citrate coated with hydroxypropylmethyl cellulose and subsequently Eudragit® E100 (a gastric juice-soluble polymer). However, since said preparation uses a gastric juice-soluble polymer as a coating agent, the release rate and bioavailability of the drug would be unfavorably affected and the onset of efficacy be hampered when a person who just finished eating or is suffering from anacidity takes the preparation.

It is known that there are many drugs of which efficacy is required to be expressed immediately after administration. For example, for the purpose of improving quality of life (QOL), a cyclic GMP (cGMP)-specific phosphodiesterase (PDE) inhibitor, especially PDE 5 inhibitor, is used as a medicament for erectile dysfunction. Such medicament preferably exerts the efficacy immediately after taking the same so that the sexual response can be controlled on demand.

However, in the case of rapid-release tablets of sildenafil citrate (Viagra tablets), which is clinically used as a PDE 5 inhibitor, it has been reported that one should take the preparation about 1 hour in advance of the time when the efficacy is expected to be expressed (WO00/24383, page 2). Besides, it has also been known a "rapidly disintegrating tablet in oral cavity" prepared by a process comprising subjecting a mixture containing sildenafil citrate and a bondable disintegrant to wet granulation followed by compression molding (JP-A 10-298062 (1998)). However, said preparation fails to mask bitterness of a drug sufficiently and hence has not been manufactured for commercialization.

DISCLOSURE OF INVENTION

There has been a demand for the development of a pharmaceutical preparation containing a medicinal substance being hardly water-soluble under neutral or alkaline conditions and being highly water-soluble under acidic conditions yet presenting unpleasant taste under such acidic conditions, which preparation rapidly disintegrates in the oral cavity without presenting unpleasant taste, shows rapid release and absorption of the medicinal substance in the digestive tract, and can achieve early onset of efficacy.

The present invention provides an intraorally rapidly disintegrating tablet containing a medicinal substance being hardly water-soluble under neutral or alkaline conditions and being highly water-soluble under acidic conditions yet presenting unpleasant taste, and a process for preparing the same.

THE BEST MODE FOR CARRYING OUT THE INVENTION

The present inventors have, in their research, found that it is possible to obtain an intraorally rapidly disintegrating tablet containing a medicinal substance being hardly water-soluble under neutral or alkaline conditions and being highly water-soluble under acidic conditions yet presenting unpleasant taste under acidic conditions, which tablet rapidly disintegrates in the oral cavity though, it does not present unpleasant taste of the substance in the oral cavity and also can facilitate the release and absorption of the medicinal substance in the digestive tract, by combining the medicinal substance with an acidic substance and coating at least one of the medicinal and acidic substances with a water-soluble coating agent being insoluble in an alcoholic solvent.

Thus, the present invention provides an intraorally rapidly disintegrating tablet having hardness of 20 N or more and porosity within the range of 25% to 50%, comprising the following ingredients:

i) a medicinal substance being hardly water-soluble under alkaline or a neutral condition and being highly water-soluble under acidic conditions yet presenting an unpleasant taste under acidic conditions;
ii) a water-soluble acidic substance;
iii) a water-soluble binding agent being soluble in alcoholic solvent; and
iv) a water-soluble saccharide,
wherein at least one of the ingredients (i) and (ii) is coated with a water-soluble coating agent being insoluble in an alcoholic solvent.

The present invention also provides a process for preparing the above-mentioned intraorally rapidly disintegrating tablet, comprising the following steps (A) to (C):

(A) preparing a substantially homogeneous mixture comprising ingredients necessary for intraorally rapidly disintegrating tablet;

(B) subjecting the mixture obtained in the step (A) above to compression under a low compression pressure; and (C) treating the tablets obtained in the compression in step (B) with an alcohol followed by drying.

The present intraorally rapidly disintegrating tablet preparation containing a medicinal substance (i), which is hardly water-soluble under neutral or alkaline conditions and is highly water-soluble under an acidic conditions yet presents unpleasant taste under acidic conditions, is characterized in that it comprises a water-soluble acidic substance (ii) so as to increase the solubility of the medicinal substance especially when administered to a subject who is suffering from anacidity or wishes to use the preparation immediately after eating; a water-soluble binding agent (iii) which is soluble in alcoholic solvent necessary for the alcoholic-solvent treatment following the compression so as to enhance the hardness of a tablet; and a water-soluble saccharide (vi) which furnishes the tablet with good solubility and sweetness; and that at least one of the medicinal substance (i) and the water-soluble acidic substance (ii) is coated with a water-soluble coating agent being insoluble in alcoholic solvent. As a result of said coating treatment, contact of a medicinal substance with an acidic substance, which is responsible to unpleasant taste, is avoidable throughout the manufacturing processes of the intraorally rapidly disintegrating tablet including not only the step (A) for mixing and the step (B) for compression molding, but also the step (C) for enhancing the hardness through dissolution and solidification of a binding agent, in the manufacture of the present intraorally rapidly disintegrating tablet.

Moreover, although the intraorally rapidly disintegrating tablet of the present invention disintegrates rapidly in the oral cavity, it can go through the cavity before the medicinal substance contacts with the acidic substance, and therefore hardly presents unpleasant taste in the oral cavity. In addition, the present preparation has advantages, for example, at the time of ingestion, no water is required for ingestion since it can disintegrate with a small amount of saliva in the oral cavity, and, after ingestion, it allows a medicinal substance to dissolve rapidly at the upper part of digestive tract (from esophagus to stomach) and the drug concentration to arise in the digestive tract thereby improving drug absorption and reducing the time until efficacy onsets.

Examples of the water-soluble acidic substance used in the preparation of the present invention include substances of which pKa is not greater than 5, preferably not greater than 4 and solubility in water at 25° C. is not less than 5 mg/mL. Preferred examples include organic acids specifically fumaric acid, tartaric acid, succinic acid, malic acid, ascorbic acid and aspartic acid. The acidic substance can be used alone or in combination of two or more substances.

Examples of the water-soluble binding agent being soluble in an alcoholic solvent include those of which solubility in both water and alcoholic solvent at 25° C. is not less than 20 mg/mL, preferably not less than 50 mg/mL. Specific examples of binding agent include polyvinyl derivatives such as polyvinylpyrrolidone (PVP), etc. and cellulose derivatives such as hydroxypropyl cellulose (HPC), etc. One or more binding agents can be used. In the present invention, binding agents having mean particle diameter of 1-100 μm, preferably 20-80 μm are used.

Examples of the water-soluble saccharide include those of which solubility in water at 25° C. is not less than 20 mg/mL, preferably not less than 50 mg/mL. Specific examples include mannitol, xylitol, erythritol, maltitol, sorbitol and lactose,. and one or more saccharides can be used. In the present invention, water-soluble saccharides having mean particle diameter of 1-100 μm, preferably 20-80 μm, more preferably 40-60 μm are used.

Examples of the water-soluble coating agent which is used for coating at least one of the medicinal substance and the water-soluble acidic substance include those of which solubility in water at 25° C. is not less than 20 mg/mL and in an alcoholic solvent at 25° C. is not greater than 1 mg/mL, such as cellulose derivatives (hydroxypropylmethyl cellulose (HPMC), methyl cellulose (MC), hydroxyethyl cellulose (HEC), etc.), polysaccharides (dextran, pullulan, sodium arginate, agar, etc.), polyalkylene oxides, polyvinyl derivatives (polyvinyl alcohol (PVA), etc.) and peptide derivatives s (gelatin, etc.). One or more coating agents among them can be used in the present invention.

It is preferable that the mean particle diameter of the medicinal substance or the water-soluble acidic substance coated with such coating agent is within the range of 30 to 500 μm, preferably 50 to 300 μm, more preferably 100 to 200 μm.

The medicinal substances to which the present invention is applicable include those being hardly water-soluble under neutral or alkaline conditions and being highly water-soluble under acidic conditions yet presenting unpleasant taste under acidic conditions. Examples of such medicinal substances include those of which solubility in water at 25° C. is not greater than 0.1 mg/mL at pH of 7 or above and is not less than 1 mg/mL at pH of 2 or below, preferably those of which solubility in water (25° C.) at pH 1.2 is not less than 10-fold, preferably not less than 100-fold compared to the solubility in water (25° C.) at pH 7.

In addition, the medicinal substances to which the present invention is applicable are those which present unpleasant taste such as bitterness, astringency, acridness, etc. under acidic conditions of, for example, pH 5 or below especially pH 4 or below, specifically, under the conditions made acidic with a water-soluble acidic substance (e.g., an acid having pKa of 5 or below, especially 4 or below) to be used in the present preparation. Examples of the acids include organic acids such as fumaric acid, tartaric acid, succinic acid, malic acid, ascorbic acid, aspartic acid, etc.

Above all, examples of medicinal substances to which the present invention is preferably applied include those which are desired to exhibit efficacy in a short time within one hour after ingestion, such as cyclic GMP-specific phosphodiesterase inhibitors.

Examples of the cyclic GMP-specific phosphodiesterase inhibitor include PDE 5 inhibitors disclosed, for example, in JP-A 09-512835 (1997), JP-A 09-503996 (1997), JP-A 2000-128883 (2000), JP-A 2000-128884 (2000), JP-A 11-505236 (1999), JP-A 11-505539 (1999), JP-A 2000-507256 (2000), JP-A 2000-503996 (2000), JP-A 2000-95759 (2000), JP-A 10-298164 (1998), JP-A 2000-72675 (2000), JP-A 2000-

72751 (2000), JP-A 09-124648 (1997), JP-A 08-231545 (1996), JP-A 08-231546 (1996), JP-A 08-253457 (2000), JP-A 11-503445 (1999), WO97/45427, JP-A 11-509221 (1999), JP-A-11-509517 (1999) and JP-A 11-509535 (1999), WO00/20033 and WO00/39099.

Preferred examples of the PDE 5 inhibitor include aromatic nitrogen-containing 6-membered cyclic compounds of the formula (I):

(I)

wherein Ring A is an optionally substituted nitrogen-containing heterocyclic group, $R^1$ is a group of the formula: —NH-Q-$R^3$ (wherein $R^3$ is an optionally substituted nitrogen-containing heterocyclic group, and Q is a loweralkylene group or a single bond), or a group of the formula: —NH—$R^4$ (wherein $R^4$ is an optionally substituted cycloalkyl group); $R^2$ is an optionally substituted aryl group, one of Y and Z is a group of the formula: =CH—, and the other is a group of the formula: =N—. See, WO01/19802 (Japan. Patent Appln. No. 277652/2000).

Examples of the nitrogen-containing heterocyclic group of the "optionally substituted nitrogen-containing heterocyclic group" for Ring A include a 5- to 10-membered monocyclic or bicyclic nitrogen-containing heterocyclic group, more particularly, a 5- or 6-membered nitrogen-containing heteromonocyclic group or a 8- to 10-membered nitrogen-containing heterobicyclic group, and most particularly, a 5- to 6-membered nitrogen-containing heteromonocyclic group shown by the formula:

or a nitrogen-containing heterobicyclic group wherein any one of above-mentioned 5- or 6-membered nitrogen-containing heteromonocyclic group is condensed with a 5- or 6-membered cyclic group, which is shown by the formula:

Examples of the nitrogen-containing heterocyclic group of the "optionally substituted nitrogen-containing heterocyclic group" for $R^3$ include a nitrogen-containing heteromonocyclic or heterobicyclic group, specifically, a non-aromatic nitrogen-containing heterocyclic group of the formula:

or an aromatic nitrogen-containing heterocyclic group of the formula:

Examples of the substituent of the "optionally substituted nitrogen-containing heterocyclic group" for Ring A include a group selected from (1) a lower alkyl group, (2) a hydroxy-substituted lower alkyl group, (3) a formyl group, (4) an oxo group, (5) an amino group, (6) a hydroxyl group, (7) a lower alkoxycarbonyl group and (8) a group selected from (i) a benzylamino group substituted by a halogen atom and a lower alkoxy group and (ii) a pyrimidinyl group substituted by a hydroxy-substituted cycloalkylcarbamoyl group.

$R^1$ is a group of the formula: —NH-Q-$R^3$ or a group of the formula: —NH—$R^4$. Examples of the substituent of the "optionally substituted nitrogen-containing heterocyclic group" for $R^3$ include a lower alkyl group, a hydroxy-substituted lower alkyl group, an oxo group, an amino group, a di-(lower alkyl)amino group, a lower alkanoyl group and a cyano-substituted lower alkyl group.

Examples of the aryl group of the "optionally substituted aryl group" for $R^2$ include a 5- to 10-membered monocyclic or bicyclic aromatic hydrocarbon group, specifically phenyl group, naphthyl group, etc.

Examples of the substituent of the "optionally substituted aryl group" for $R^2$ include a lower alkoxy group, a halogen atom, a cyano group, etc.

Examples of the substituent of the "optionally substituted cycloalkyl group" for $R^4$ include a lower alkoxy group, hydroxyl group, morpholinyl group, etc.

Throughout the present description and claims, the "lower alkyl group" means a straight chain or branched chain alkyl group having 1 to 6 carbon atoms, such as methyl, ethyl, propyl, isopropyl, butyl, isobutyl, tert-butyl, etc. The "lower alkoxy group" means a straight chain or branched chain alkoxy group having 1 to 6 carbon atoms, such as methoxy, ethoxy, propoxy, isopropyloxy, butyloxy, isobutyloxy, tert-butyloxy, etc. The "cycloalkyl group" means a cycloalkyl having 3 to 8 carbon atoms, such as cyclopropyl, cyclobutyl, cyclopentyl, cyclohexyl, cycloheptyl, etc. The "lower alkylene group" means a straight chain or branched chain alkylene group having 1 to 6 carbon atoms, such as methylene, ethylene, trimethylene, etc.

The intraorally rapidly disintegrating tablet of the present invention is preferably applicable to a medicinal substance in the free form, which shows disadvantages in terms of taste, stability or operability when converted into an acid addition salt.

Among the PDE 5 inhibitors used herein, especially preferable examples include the following compounds.

(S)-2-(2-hydroxymethyl-1-pyrrolidinyl)-4-(3-chloro-4-methoxybenzylamino)-5-[N-(2-pyrimidinylmethyl)-carbamoyl]pyrimidine;

(S)-2-(2-hydroxymethyl-1-pyrrolidinyl)-4-(3-chloro-4-methoxybenzylamino)-5-[N-(2-morpholinoethyl)-carbamoyl]pyrimidine;

2-(5,6,7,8-tetrahydroimidazo[1,2-a]pyrazin-7-yl)-4-(3-chloro-4-methoxybenzylamino)-5-[N-(2-pyrimidinylmethyl)-carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]-pyrimidine;

(S)-2-(2-hydroxymethyl-1-pyrrolidinyl)-4-(3-chloro-4-methoxybenzylamino)-5-[N-(5-pyrimidinylmethyl)carbamoyl]-pyrimidine;

(S)-2-[N-(2-pyrimidinylmethyl)carbamoyl]-3-(3-chloro-4-methoxybenzylamino)-5-[2-hydroxymethyl-1-pyrrolidinyl]-pyrazine;

(S)-2-[N-(2-morpholinoethy)carbamoyl]-3-(3-chloro-4-methoxybenzylamino)-5-(2-hydroxymethyl-1-pyrrolidinyl)-pyrazine; and (S)-2-(2-hydroxymethyl-1-pyrrolidinyl)-4-(3-chloro-4-methoxybenzylamino)-5-[N-(1,3,5-trimethyl-4-pyrazolyl)-carbamoyl]pyrimidine.

The present intraorally rapidly disintegrating tablets may contain additives generally used in the pharmaceutical solid preparations. Examples of the additives include excipients such as calcium citrate, calcium phosphate, crystalline cellulose and magnesium aluminometasilicate, etc.; disintegrants such as corn starch, potato starch, sodium carboxymethyl starch, partially pregelatinized starch, calcium carboxymethylcellulose, carboxymethyl-cellulose, low-substituted hydroxypropylcellulose, cross-linked sodium carboxymethyl-cellulose, cross-linked polyvinylpyrrolidone, etc.; lubricants such as magnesium stearate, calcium stearate, talc, light anhydrous silicic acid, hydrous silica dioxide, etc.; flavors such as orange oil, fennel oil, cinnamon oil, clove oil, turpentine oil, peppermint oil, eucalyptus oil, etc.; colorants such as Food Color Red Nos. 2 and 3, Food Color Yellow Nos. 4 and 5, Food Color Green No. 3, Food Color Blue Nos. 1 and 2, and aluminum lakes of these Food Colors, iron sesquioxide, yellow iron sesquioxide, etc.; sweetenings such as saccharine, aspartame, Stevia, etc.; taste adjusting agent such as sodium chloride, etc.; solubilizing agents such as cyclodextrin, arginine, lysine, tris-aminomethane, etc., and the like. It is preferable to compound a lubricant in a small amount, when it is used.

The formulated amount of respective ingredients in the present intraorally rapidly disintegrating tablet expressed in the content (w/w %) of each ingredient to the total weight of the tablet, that is, $$\frac{\text{weight of each ingredient (g)}}{\text{total weight of tablet (g)}} \times 100$$

is shown below, wherein "%" means "w/w %".

A medicinal substance: 1-70%, preferably 5-50%, more preferably 10-30%.

A water-soluble acidic substance: 0.1-50%, preferably 1-30%.

A water-soluble saccharide: 5-95%, preferably 10-85%, more preferably 30-80%.

A water-soluble binding agent: 0.1-30%, preferably 1-10%.

A water-soluble coating agent: 0.02-10%, preferably 0.1-6%.

The present intraorally rapidly disintegrating tablets have the following properties.

Disintegration time in the oral cavity: within 60 seconds, preferably 45 seconds, and more preferably 30 seconds.

Degree of hardness: 20 N (Newton) or above, preferably, 30 N or above, wherein 20 N is the requisite hardness for pushing a tablet out of a blister package (press through package: PTP)

Porosity (%): 25-50%, preferably 30-45%, when determined according to the following equation:

$$\text{Porosity}(\%) = \frac{(V \times \rho) - M}{V \times \rho} \times 100$$

V: volume of tablet (mL)
$\rho$: true density of tablet excluding pore (g/mL)
M: weight of tablet (g)

Drug dissolution rate: 70% and over, preferably 80% and over for initial 30 minutes when determined by the dissolution test Method 2 (Paddle method, XII revision of Japanese Pharmacopoeia) under the conditions of paddle rotation of 50 rpm and 37° C. in water.

The intraorally rapidly disintegrating tablets of the present invention can be prepared by the afore-mentioned method comprising steps (A), (B) and (C). The details of the method are illustrated bellow.

Step (A): Preparation of Homogeneous Mixture of Ingredients

The preparation of said mixture involves processes of granulating the ingredients after mixing them successively or granulating the ingredients simultaneously to yield granules for compression. The mixing process can be carried out by any of conventional methods known in the field of pharmaceuticals by means of, for example, a double-corn mixer (Double-Corn Mixer manufactured by Yashima Chemical Engineering Co., Ltd.), a fluidized-bed granulator (Multiplex manufactured by Powrex Corporation; Spirer Flow manufactured by Freund Co., Ltd.), a high-shear mixer granulator (High-Speed Mixer manufactured by Fukae-Powtech Co.; Vertical Granulator manufactured by Powrex Corporation) or a vibrating screen (vibrating screen manufactured by Dalton), and the like.

In the present step, the ingredients (i)-(iv) are mixed successively. Before mixing, either or both of the ingredients (i) and (ii) are coated with a water-soluble coating agent being insoluble in alcoholic solvent, followed by:

(a) when one of the ingredients (i) and (ii) is coated with a water-soluble coating agent, admixing the uncoated ingredient (i) or (ii) with the ingredient (iv), granulating the mixture while adding the ingredient (iii) or an aqueous solution thereof, drying the resultant granules, if necessary, and mixing the coated ingredient (i) or (ii); or (b) when both of the ingredients (i) and (ii) are coated with a water-soluble coating agent, granulating ingredient (iv) while adding the ingredient (iii) or an aqueous solution thereof, drying the resultant granules, if necessary, and mixing the coated ingredients (i) and (ii) to the resultant granules.

The granulation can be carried out by any one of conventional granulation techniques such as wet granulation, layering granulation or dry granulation.

The wet granulation can be carried out by subjecting the ingredient (iv) (and an uncoated ingredient(s) of ingredients (i) and (ii)) to be granulated to stirring and granulation with a mixer granulator or a high-shear mixer granulator, etc., while adding an aqueous solution of ingredient (iii). Alternatively, the ingredients to be granulated are combined with an aqueous solution of a binder, kneaded, and subjected to granulation with an extrusion granulator and sizing. In still alternative process, an aqueous solution of a binder is sprayed to the mixture of ingredients with a fluidized bed granulator, a rotary fluidized bed granulator, etc.

The layering granulation can be carried out by adding ingredient (iv) (and uncoated ingredient(s) of ingredients (i) and (ii)) to be granulated to a rolling inactive carriers while spraying an aqueous solution of ingredient (iii) with a centrifugal fluidized bed granulator or the like to make the mixture of ingredients adhere to the carries. Examples of the inactive carrier that used in this process include crystals of sugars or inorganic salts such as crystalline lactose, crystalline cellulose, crystalline sodium chloride, etc., and spherical granules such as spherical granules of purified white sugar (brand name: Nonpareil-103, Freund Co., Ltd.), spherical granules of lactose and pregelatinized starch, etc.

The dry granulation can be carried out mixing ingredient (iii) with ingredient (iv) (and uncoated ingredient(s) of ingredients (i) and (ii)) to be granulated, followed by granulation with a roller compactor, a roll granulator, etc.

The coating of ingredient (i) and/or (ii) with a water-soluble coating agent being insoluble in alcoholic solvent can be carried out by granulating said ingredient (i) or (ii) while adding an aqueous solution or aqueous alcohol solution of a water-soluble coating agent being insoluble in alcoholic solvent, thereby coating the surface of granules of ingredient (i) and/or (ii) with the water-soluble coating agent and, if necessary, spraying an aqueous solution of said water-soluble coating agent being insoluble in alcoholic solvent. In this process, it is preferred to add an anti-adhesion agent such as talc to prevent agglomeration of coated particles and to regulate the dissolution rate of the water-soluble coating agent in oral cavity.

Step (B): Compression of the Mixture Obtained in Step (A) Under Low Pressure

The compression of the mixture obtained in Step (A) can be carried out by using a conventional tableting machine such as a rotary three-layer tableting machine (RT-3L-14; Kikusui Seisakusyo, Ltd.) or a dual tableting machine (Correct D65RC; Kikusui Seisakusyo, Ltd.), and the like, under the condition of compressing pressure of 5-40 MPa, preferably 7-20 MPa. When tableting, for the purpose of preventing possible troubles such as sticking, a method wherein a lubricant is supplied to the compression by compressing a mixture of a lubricant (e.g., magnesium stearate, calcium stearate) and a fluidizing agent (e.g., crystalline cellulose), and a mixture obtained in step (A) to the molding by turns (JP-A 10-29806 (1998)) can be applicable. Alternatively, a method wherein compression is carried out with spraying a lubricant powder to the compression punch (JP-B 41-1273 (1966), JP-B 48-20103 (1973)), or a method wherein compression is carried out through a polymer film for preventing adhesion (JP-A 08-19589 (1996)) can be also applicable.

Step (C): Alcoholic-solvent-treatment and Drying of Tablets Obtained by Compression in Step (B)

Treatment with an alcoholic solvent can be carried out, for example, by allowing the tablets to stand under atmosphere of an alcoholic solvent or by spraying vapor of the alcoholic solvent to the tablets. The vapor of the alcoholic solvent can be produced by spraying the alcoholic solvent with heating. It is preferable to maintain the vapor at a temperature of 60° C. or below, more preferably 40° C. or below, in consideration of stability of the medicinal substance.

Since a binding agent contained in the tablets dissolves when treated with vapor of an alcoholic solvent, the dissolution amount of the binding agent can be increased, within a certain limit, by extending the processing time, which in turn enhances hardening by drying treatment in the next step. In the case where the requisite hardness cannot be achieved or the disintegration time is prolonged, the amount of the binding agent, the processing time, the amount of alcohol vapor to be sprayed, and the like, should be selected appropriately depending on the intended hardness and/or disintegration time.

The objective intraorally rapidly disintegrating tablets can be obtained by removing the alcoholic solvent from the resultant products of the treatment above. The removal of the alcoholic solvent may be carried out by allowing the products to stand at room temperature under atmospheric condition, or under reduced pressure, heating or ventilation in order to promote the removal of the alcoholic solvent.

The alcoholic solvent usable includes those of which boiling point is not higher than 85° C., for example, a lower alcohol such as methanol, ethanol, isopropanol, etc.

The tablet rapidly disintegrating in oral cavity of the present invention may be molded in a shape of tablet form, oval form, spherical form or squared form and the volume thereof is within 0.05 to 1 mL/unit, preferably 0.1 to 0.5 mL.

The compound (I) used as a preferred medicinal substance (PDE 5 inhibitor) in the present invention can be prepared by reacting a compound of the formula (II):

(II)

wherein $X^1$ is a halogen atom, $R^5$ is a protecting group of carboxy group, and the other symbols are the same as defined above with a compound of the formula (III):

(III)

wherein the symbols are the same as defined above to prepare a compound of the formula (IV):

(IV)

wherein the symbols are the same as defined above;

oxidizing the product (IV) to prepare a methylsulphonyl (or methylsulfinyl) compound of the formula (V):

(V)

wherein n is an integer of 1 or 2, and the other symbols are the same as defined above;

reacting the compound (V) with a compound of the formula (VI):

(VI)

wherein the symbols are the same as defined above or a salt thereof to prepare a compound of the formula (VII):

(VII)

wherein the symbols are the same as defined above;

removing the carboxyl-protecting group $R^5$ to prepare a compound of the formula (VIII):

(VIII)

wherein the symbols are the same as defined above; and reacting the compound (VIII) with a compound of the formula (IX-a):

(IX-a)

wherein $R^1$ is the same as defined above.

Besides, the compound (I) can be prepared by:

a) halogenating the compound (VIII) to prepare a compound of the formula (X):

(X)

wherein $X^2$ is a halogen atom and the other symbols are the same as defined above and b) reacting the compound (X) with the compound (IX-a).

Meanwhile, the compound (VII) can be also prepared by treating a di-halogenated compound of the formula (XI):

(XI)

wherein $X^3$ and $X^4$ are a halogen atom, and the other symbols are the same as defined above with carbon dioxide to prepare a compound of the formula (XII):

(XII)

wherein the symbols are the same as defined above, protecting a carboxy group of the compound (XII) to prepare a compound of the formula (XIII):

(XIII)

wherein the symbols are the same as defined above, reacting the compound (XIII) with the compound (III) to prepare a compound of the formula (XIV):

wherein the symbols are the same as defined above and reacting the compound (XIV) with the compound (VI).

Moreover, the compound (XIV) can be also prepared by hydrolyzing the compound (V) to prepare a compound (XV) of the formula:

wherein the symbols are the same as defined above and halogenating the compound (XV).

The reaction of the compound (II) with (III) is carried out in the presence or absence of an acid scavenger in a solvent. The acid scavenger includes, for example, an organic base such as N,N-diisopropylethylamine, N-methylmorpholine, triethylamine and pyridine, and an inorganic base such as sodium hydride, sodium carbonate, potassium carbonate and sodium hydrogen carbonate. The solvent may be any solvent which do ndt disturb thereaction, for example, N,N-dimethylformamide, tetrahydrofuran, toluene, ethyl acetate, chloroform, dimethoxyethane, xylene or dimethylsulfoxide. The reaction is carried out at a temperature of from $-10°$ C. to room temperature, preferably at a temperature of from $0°$ C. to room temperature.

The reaction of oxidizing the compound (IV) to give the methyl sulfonyl (or methyl sulfinyl) compound (V) is carried out in the presence of an oxidizing agent in a solvent. The oxidizing agent includes, for example, peracids such as m-chloroperbenzoic acid or peracetic acid or an inorganic oxidizing agent such as manganese dioxide, sodium periodate, hydrogen peroxide, acid nitrates, dinitrogen tetroxide, halogens, N-halogenated compounds, hydroperoxide, iodobenzene acetate, t-butyl hypochlorite, sulfuryl chloride or potassium peroxymonosulphate. The solvent may be any solvent which does not disturb the reaction, for example, chloroform, methylene chloride, dichloroethane and acetic acid. The reaction carried out at a temperature of from $-78°$ C. to $50°$ C., preferably at a temperature of from $-10°$ C. to $10°$ C.

The reaction of the compound (V) with the compound (VI) or a salt thereof can be carried out in the presence or absence of an acid scavenger in a solvent. The acid scavenger includes, for example, an organic base such as N,N-diisopropylethylamine, N-methylmorpholine, triethylamine and pyridine, and an inorganic base such as sodium hydride, sodium carbonate, potassium carbonate and sodium hydrogen carbonate. The salt of the compound (VI) is preferably an alkali metal salt such as sodium salt, potassium salt. The solvent may be any solvent which does not disturb the reaction, for example, N,N-dimethylformamide, tetrahydrofuran, dimethoxyethane or dimethylsulfoxide. The reaction is carried out at a temperature of from $0°$ C. to $150°$ C., preferably at a temperature of from room temperature to $60°$ C.

The reaction of removing the protecting group $R^5$ for a carboxyl group of the compound (VII) to give the compound (VIII) can be carried out by a conventional method such as hydrolysis or catalytic reduction which is selected according to the types of the protecting group for a carboxyl group to be removed. When a protecting group for a carboxyl group is removed by hydrolysis, the hydrolysis is carried out, for example, in the presence or absence of a base in a solvent. The base is preferably, for example, an alkali metal hydroxide such as sodium hydroxide, potassium hydroxide or lithium hydroxide, an alkali metal carbonate such as sodium carbonate or potassium carbonate. The solvent may be water or a mixture of water and methanol, ethanol, tetrahydrofuran, dioxane, N,N-dimethylformamide or dimethylsulfoxide. The reaction is carried out at a temperature of from $0°$ C. to $80°$ C., preferably at a temperature of from $5°$ C. to $60°$ C. The protecting group for a carboxyl group represented by $R^5$ may be any conventional protecting group for carboxyl group such as a lower alkyl group or benzyl group.

The reaction of the compound (VIII) with the compound (IX-a) can be carried out in the presence or absence of a condensing agent, a base or an activating agent in suitable solvent. The condensing agent includes, for example, dicyclohexylcarbodiimide, 1-ethyl-3-(3-dimethylaminopropyl) carbodiimide, diphenylphosphoryl azide or diethylcyanophosphonate, which is usually used in the peptide synthesis. The base includes, for example, an organic base such as triethylamine or N-methylmorpholine, and the activating agent includes, for example, 1-hydroxybenzotriazole. The solvent may be any solvent which does not disturb the reaction, for example, methylene chloride, tetrahydrofuran, N,N-dimethylformamide, acetonitrile, N,N-dimethylacetamide or ethyl acetate. The reaction is carried out at a temperature of from $-30°$ C. to $50°$ C., preferably at a temperature of from $-10°$ C. to $10°$ C.

The alternative process of converting the compound (VIII) into the compound (X), which is further reacted with the compound (IX-a) can be carried out by firstly reacting the compound (VIII) with a halogenating agent in the presence or absence of an activating agent by a conventional method, and reacting the resultant compound (X) with the compound (IX-a). The reaction of the compound (VIII) with a halogenating agent is carried out in a solvent. This halogenating agent is preferably thionyl chloride, oxalyl chloride or phosphorus pentachloride. The activating agent is preferably an amide compound such as N,N-dimethylformamide. The solvent may be any solvent which does not disturb the reaction, for example, methylene chloride, chloroform, tetrahydrofuran, benzene, toluene or dioxane. The reaction is carried out at a temperature of from $-30°$ C. to $100°$ C., preferably at a temperature of from $-5°$ C. to $10°$ C.

The subsequent reaction of the compound (X) with the compound (IX-a) can be carried out in the presence or absence of an acid scavenger in a solvent. The acid scavenger includes, for example, an organic base such as N,N-diisopropylethylamine, N-methylmorpholine, triethylamine, pyridine, dimethylaminopyridine, and an inorganic base such as sodium hydride, sodium carbonate, potassium carbonate, sodium hydrogen carbonate. The solvent may be any solvent which does not disturb the reaction, for example, tetrahydrofuran, methylene chloride, chloroform, toluene, benzene, dioxane, ethyl acetate. The reaction is carried out at a temperature of from $-30°$ C. to $100°$ C., preferably at a temperature of from $-5°$ C. to $10°$ C.

The treatment of the dihalogeno compound (XI) with the carbon dioxide to give the compound (XII) can be carried out in the presence of a base in a solvent. The base includes, for example, an alkali metal salt of an organic base such as lithium diisopropylamide, lithium 2,2,6,6-tetramethylpiperidide. The solvent may be any solvent which does not disturb the reaction, for example, tetrahydrofuran, 1,2-dimethoxyethane, diethyl ether. The reaction is carried out at a temperature of from −100° C. to −30° C., preferably at a temperature of from −100° C. to −70° C.

The reaction of protecting the carboxyl group of the compound (XII) to give the compound (XIII) can be carried out by a conventional method, for example, by reacting with an alkylating agent in the presence of a base in a solvent, when the protecting group is a lower alkyl group. The alkylating agent is preferably a lower alkyl halide such as methyl iodide. The base is preferably an alkali metal hydrogen carbonate, and the solvent may be any solvent which does not disturb the reaction, for example, N,N-dimethylformamide, tetrahydrofuran. The reaction is carried out at a temperature of from 0° C. to 100° C., preferably at a temperature of from a room temperature to 70° C.

The reaction of the compound (XIII) with the compound (III) to give the compound (XIV) can be carried out in the same manner as in the reaction of the compound (II) with the compound (III).

The reaction of the compound (XIV) with the compound (VI) to give the compound (VII) can be carried out in the same manner as in the reaction of the compound (V) with the compound (VI).

The hydrolysis of the compound (V) to give the compound (XV) can be carried out in the presence or base in a solvent. The base includes, for example, an alkali metal hydroxide such as sodium hydroxide, potassium hydroxide, potassium hydroxide or lithium hydroxide, and an alkali metal carbonate such as sodium carbonate or potassium carbonate. The solvent is preferably water, or a mixture of water and methanol, ethanol, tetrahydrofuran, dioxane, N,N-dimethylformamide or dimethylformamide. The reaction is carried out at a temperature of from −20° C. to 80° C., preferably at a temperature of from −5° C. to 60° C.

The reaction of halogenating the compound (XV) to give the compound (XIV) can be carried out in the same manner as in the reaction of preparing the compound (X) by halogenating the compound (VIII) by a halogenating agent.

EXAMPLE 1

(1) The compound of the following formula having PDE 5 inhibitory activity (mean particle diameter: 10 µm; 50 g) and mannitol (Japanese Pharmacopoeia grade, hereinafter, "JP grade", mean particle diameter: 50 µm; 217.1 g; Nikken Chemical Industry) are subjected to a fluidized-bed granulator (Multiplex MP-01/03; Powrex Corporation), and thereto is sprayed a 5 w/w% aqueous solution (90 g) of PVP (JP grade, PVP-k30; BASF) at 5 g/min for 18 minutes while controlling the inlet-air temperature at 50° C. After spraying, the inlet-air temperature is adjusted to 70° C. and the resultant granules are dried until the temperature thereof becomes 40° C. to give granules of active ingredient.

(2) Fumaric acid (Japanese pharmaceutical excipient standard, mean particle diameter: 10 µm; 200 g; Fuso Chemical Industry) is subjected to a fluidized-bed granulator (Multiplex MP-01/03; Powrex Corporation), and thereto is sprayed a 6 w/w% aqueous solution (100 g) of HPMC (JP grade, HPMC TC-5EW; Shin-Etsu Chemical, Co. Ltd.) at 5 g/min for 20 minutes while controlling the inlet-air temperature at 50° C. After completion of spraying of the aqueous solution, a mixture of HPMC (40 g), talc (JP grade, 8 g; Nippon Talc), ethanol (526.4 g) and water (225.6 g) is sprayed at 5 g/min for 160 minutes while controlling the inlet-air temperature at 60° C. After completion of spraying, the inlet-air temperature is adjusted to 70° C. and the resultant granules are dried until the temperature thereof becomes 40° C. to give HPMC-coated granules of fumaric acid.

(3) The granules (244.44 g) of active ingredient obtained in (1), the granules (22.86 g) of fumaric acid obtained in (2) and aspartame (Japanese pharmaceutical excipient standard, Chemical name: N-L-α-aspartyl-L-phenylalanine, 2.7 g, mean particle diameter: 10 µm; Ajinomoto, co., Ltd.) are subjected to a double corn mixer (volume: 2 litter; Yashima Chemical Engineering Co., Ltd.) and mixed at 55 rpm for 3 minutes to give granules for tableting.

(4) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm).After discharging the tablets, the granules for tableting obtained in (3) are compressed in the main compression part at the compressing pressure of 10 MPa to give tablets (300 mg/tablet).

(5) The tablets prepared in (4) are allowed to stand for 12 hours at 25° C. in a desiccator filled with ethanol vapor, and then maintained in a box-type dryer at 45° C. for 5 hours to remove ethanol to give intraorally rapidly disintegrating tablets (300 mg/tablet).

EXAMPLE 2

(1) A compound (50 g) described in EXAMPLE 1(1) and mannitol (JP grade, mean particle diameter: 50µm, 213.45 g, Nikken Chemical) are subjected to granulation with a high-shear mixer granulator (ultra-slim High-speed Mixer; Fukae-Powtex) while adding a 18 w/w% aqueous solution of HPC (24.5 g, HPC SL; Nippon Soda). After granulation, the granules are dried in a box type drier at 45° C. for 8 hours, sized and sieved through a No. 22 Sieve (710 µm) to give granules of active ingredient.

(2) The granules (214.36 g) of active ingredient obtained in (1), the granules (15.24 g) of fumaric acid obtained in EXAMPLE 1, (2) and aspartame (Japanese Standard of Food Additives, Chemical name: N-L-α-aspartyl-L-phenylalanine, 2.4 g, mean particle diameter: 10 µm; Ajinomoto, Co. Ltd.) are subjected to a double corn mixer (volume: 2 litter; Yashima Chemical Engineering Co., Ltd.) and mixed at 55 rpm for 3 minutes to give granules for tableting.

(3) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in (2) are compressed in the main compression part at the compressing pressure of 10 MPa to give tablets (290 mg/tablet).

(4) The tablets prepared in (3) are allowed to stand for 12 hours at 25° C. in a desiccator filled with ethanol vapor, and then maintained in a box-type dryer at 45° C. for 5 hours to remove ethanol to give intraorally rapidly disintegrating tablets (290 mg/tablet).

EXAMPLE 3

(1) A compound (50 g) described in EXAMPLE 1 (1) and erythritol (Japanese pharmaceutical excipient standard, mean particle diameter: 60 μm; 217.1 g; Nikken Chemical Industry) are subjected to a fluidized-bed granulator (Multiplex MP-01/03; Powrex Corporation), and thereto is sprayed a 5 w/w% aqueous solution (90 g) of PVP (JP grade, PVP-k30; BASF) at 5 g/min for 18 minutes while controlling the inlet-air temperature at 50° C. After spraying, the inlet-air temperature is adjusted to 70° C. and the resultant granules are dried until the temperature thereof becomes 40° C. to give granules of active ingredient.

(2) The granules (244.44 g) of active ingredient obtained in (1), the granules (22.86 g) of fumaric acid obtained in EXAMPLE 1 (2) and aspartame (Japanese Standard of Food Additives, Chemical name: N-L-α-aspartyl-L-phenylalanine, 2.7 g, mean particle diameter: 10 μm; Ajinomoto, co., Ltd.) are subjected to a double corn mixer (volume: 2 litter; Yashima Chemical Engineering Co., Ltd.) and mixed at 55 rpm for 3 minutes to give granules for tableting.

(3) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in (2) are compressed in the main compression part at the compressing pressure of 10 MPa to give tablets (300 mg/tablet).

(4) The tablets prepared in (3) are allowed to stand for 12 hours at 25° C. in a desiccator filled with ethanol vapor, and then maintained in a box-type dryer at 45° C. for 5 hours to remove ethanol to give intraorally rapidly disintegrating tablets (300 mg/tablet).

EXAMPLE 4

(1) A compound (50 g) described in EXAMPLE 1 (1) and erythritol (Japanese pharmaceutical excipient standard, mean particle diameter: 60 μm; 212.8 g; Nikken Chemical Industry) are subjected to a fluidized-bed granulator (Multiplex MP-01/03; Powrex Corporation), and thereto is sprayed a 5 w/w% aqueous solution (90 g) of PVP (JP grade, PVP-k30; BASF) at 5 g/min for 18 minutes while controlling the inlet-air temperature at 50° C. After spraying, the inlet-air temperature is adjusted to 70° C. and the resultant granules are dried until the temperature thereof becomes 40° C. to give granules of active ingredient.

(2) The granules (240.57 g) of active ingredient obtained in (1) and the granules (11.43 g) of fumaric acid obtained in EXAMPLE 1 (2) are subjected to a double corn mixer (volume: 2 litter; Yashima Chemical Engineering Co., Ltd.) and mixed at 55 rpm for 3 minutes to give granules for tableting.

(3) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 8 mm; spherical curvature radius: 10 mm). After discharging the tablets, the granules for tableting obtained in (2) are compressed in the main compression part at the compressing pressure of 10 MPa to give tablets (140 mg/tablet).

(4) The tablets prepared in (3) are allowed to stand for 12 hours at 25° C. in a desiccator filled with ethanol vapor, and then maintained in a box-type dryer at 45° C. for 5 hours to remove ethanol to give intraorally rapidly disintegrating tablets (140 mg/tablet).

EXAMPLE 5

(1) A compound (mean particle diameter: 10 μm, 100 g) described in EXAMPLE 1 (1) and mannitol (JP grade, mean particle diameter: 50 μm, 403.8 g, Nikken Chemical) are subjected to a fluidized-bed granulator (Multiplex MP-01; Powrex Corporation), and thereto is sprayed a 5 w/w% aqueous solution (180 g) of PVP (JP grade, PVP-k30; BASF) at 9 g/min for 20 minutes while controlling the inlet-air temperature at 50° C. After spraying, the inlet-air temperature is adjusted to 70° C. and the resultant granules are dried until the temperature thereof becomes 40° C. to give granules of active ingredient.

(2) Fumaric acid (Japanese pharmaceutical excipient standard, mean particle diameter: 80 μm; 400 g; Fuso Chemical Industry) is subjected to a fluidized-bed granulator (Multiplex MP-01; Powrex Corporation), and thereto is sprayed a 6 w/w% aqueous solution (200 g) of HPMC (JP grade, HPMC TC-5EW; Shin-Etsu Chemical, Co. Ltd.) at 8 g/min for 25 minutes while controlling the inlet air temperature at 50° C. After completion of spraying, the inlet-air temperature is adjusted to 70° C. and the resultant granules are dried until the temperature thereof becomes 40° C. to give HPMC-coated granules of fumaric acid.

(3) The granules (410.24 g) of active ingredient obtained in (1), the granules (32.96 g) of fumaric acid obtained in (2) and aspartame (Japanese Standard of Food Additives, Chemical name: N-L-α-aspartyl-L-phenylalanine, 4.8 g, mean particle diameter: 10 μm; Ajinomoto, co., Ltd.) are subjected to a double corn mixer (volume: 2 litter; Yashima Chemical Engineering Co., Ltd.) and mixed at 55 rpm for 3 minutes to give granules for tableting.

(4) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in (3) are compressed in the main compression part at the compressing pressure of 10 MPa to give tablets (280 mg/tablet).

(5) The tablets prepared in (4) are allowed to stand for 12 hours at 25° C. in a desiccator filled with ethanol vapor, and then maintained in a box-type dryer at 45° C. for 5 hours to remove ethanol to give intraorally rapidly disintegrating tablets (280 mg/tablet).

EXAMPLE 6

Intraorally rapidly disintegrating tablets are prepared in the same manner as described in EXAMPLE 1 except that 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine is used as a PDE 5 inhibitor in EXAMPLE 1 (1).

EXAMPLE 7

Intraorally rapidly disintegrating tablets are prepared in the same manner as described in EXAMPLE 1 except that 2-(5, 6,7,8-tetrahydro-1,7-naphthyridin-7-yl)-4-(3-chloro-4-methoxybenzylamino)-5-[N-(2-molphorinoethyl)-carbamoyl]pyrimidine is used as a PDE 5 inhibitor in EXAMPLE 1 (1).

EXAMPLE 8

Intraorally rapidly disintegrating tablets are prepared in the same manner as described in EXAMPLE 1 except that (S)-2-(2-hydroxymethyl-1-pyrolidinyl)-4-(3-chloro-4-methoxybenzylamino)-5-[N-(5-pyrimidinylmethyl)-carbamoyl]pyrimidine is used as a PDE 5 inhibitor in EXAMPLE 1 (1).

REFERENCE EXAMPLE 1

Preparation Without Alcoholic-solvent Treatment

Tablets (300 mg/tablet) are prepared in the same manner as described in EXAMPLE 1 (1)-(4) (ethanol-treatment of EXAMPLE 1 (5) is omitted).

REFERENCE EXAMPLE 2

Preparation Under Compressing Conditions for Improving Hardness

A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in EXAMPLE 1 (3) are compressed in the main compression part at the compressing pressure of 50 MPa to give tablets (300 mg/tablet).

REFERENCE EXAMPLE 3

Preparation with Uncoated Fumaric Acid (1) A compound (mean particle diameter: 10 µm; 75 g) described in EXAMPLE 1 (1), mannitol (JP grade, mean particle diameter: 50 µm, 338.25 g, Nikken Chemical) and fumaric acid (Japanese pharmaceutical excipient standard, mean particle diameter: 10 µm; 30 g; Fuso Chemical Industry) are put into a high-shear mixer granulator (ultra-slim High-speed Mixer; Fukae-Powtex) and granulated while adding a 15 w/w% aqueous solution (45 g) of PVP (JP grade, PVP-k30; BASF). After granulation, the granules are dried in a box type drier at 45° C. for 6 hours, sized and sieved through a No. 22 Sieve (710 µm) to give granules for tableting.

(2) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in (1) are compressed in the main compression part at the compressing pressure of 10 MPa to give tablets (300 mg/tablet).

REFERENCE EXAMPLE 4

Preparation with Uncoated Fumaric Acid and with Ethanol-treatment

The tablets prepared in REFERENCE EXAMPLE 3 (2) are allowed to stand for 12 hours at 25° C. in a desiccator filled with ethanol vapor, and then maintained in a box-type dryer at 45° C. for 5 hours to remove ethanol to give intraorally rapidly disintegrating tablets (300 mg/tablet).

REFERENCE EXAMPLE 5

Preparation without Fumaric Acid (1) A compound (mean particle diameter: 10 µm; 50 g) described in EXAMPLE 1 (1) and mannitol (JP grade, mean particle diameter: 50 µm, 247 g, -Nikken Chemical) are subjected to a fluidized-bed granulator (Multiplex MP-01/03; Powrex Corporation), and thereto is sprayed an aqueous solution (60 g) of a 5 w/w% of PVP (JP grade, PVP-k30; BASF) at 5 g/min for 12 minutes while controlling the inlet-air temperature at 50° C. After spraying, the inlet-air temperature is adjusted to 70° C. and the resultant granules are dried until the temperature thereof becomes 40° C. to give granules of active ingredient.

(2) A separately prepared mixture of magnesium stearate (9 parts) and crystalline cellulose (1 part) is compressed with a rotary three-layer tableting machine (RT-3L-14, Kikusui Seisakusyo Ltd.) in the first preliminary compression part to make magnesium stearate adhere to punch (diameter: 10 mm; spherical curvature radius: 13 mm). After discharging the tablets, the granules for tableting obtained in (1) are compressed in the main compression part at the compressing pressure of 10 MPa to give tablets (300 mg/tablet).

REFERENCE EXAMPLE 6

Preparation without Fumaric Acid and with Ethanol Treatment

The tablets prepared in REFERENCE EXAMPLE 5 (2) are allowed to stand for 12 hours at 25° C. in a desiccator filled with ethanol vapor, and then maintained in a box-type dryer at 45° C. for 5 hours to remove ethanol to give intraorally rapidly disintegrating tablets (300 mg/tablet).

EXPERIMENT 1

Measurement of Hardness

Hardness of each tablet obtained in EXAMPLES 1 to 5 and REFERENCE EXAMPLES 1 to 6 was determined as the force required for breaking the tablet using a tablet hardness tester (Tablet Tester 6D; Schleuniger). Measurement was performed in 5 runs and a mean value was calculated. The results are shown in the following Tale 1.

TABLE 1

| Specimen for measurement, A tablet obtained in: | Hardness (N) |
| --- | --- |
| EXAMPLE 1 | 45 |
| EXAMPLE 2 | 40 |
| EXAMPLE 3 | 45 |
| EXAMPLE 4 | 38 |
| EXAMPLE 5 | 46 |
| REFERENCE EXAMPLE 1 | 11 |
| REFERENCE EXAMPLE 2 | 43 |
| REFERENCE EXAMPLE 3 | 10 |
| REFERENCE EXAMPLE 4 | 45 |
| REFERENCE EXAMPLE 5 | 10 |
| REFERENCE EXAMPLE 6 | 50 |

EXPERIMENT 2

Measurement of Porosity

The weight (M) of each tablet obtained in EXAMPLES 1 to 5 and REFERENCE EXAMPLES 1 to 6 was measured. Besides, the volume (V) of each tablet was measured with a micrometer (Digitrix II; NSK) and the density (ρ) of the tablet other than void space with a pycnometer (Autopycnometer Type 1320; Micrometric). The porosity of each tablet was calculated according to the following equation.

$$\text{Porosity}(\%) = \frac{(V \times \rho) - M}{V \times \rho} \times 100$$

TABLE 2

| Specimen for measurement, A tablet obtained in: | Porosity (%) |
|---|---|
| EXAMPLE 1 | 35 |
| EXAMPLE 2 | 34 |
| EXAMPLE 3 | 33 |
| EXAMPLE 4 | 31 |
| EXAMPLE 5 | 34 |
| REFERENCE EXAMPLE 1 | 35 |
| REFERENCE EXAMPLE 2 | 22 |
| REFERENCE EXAMPLE 3 | 35 |
| REFERENCE EXAMPLE 4 | 35 |
| REFERENCE EXAMPLE 5 | 33 |
| REFERENCE EXAMPLE 6 | 33 |

EXPERIMENT 3

Evaluation of Disintegration Time in the Oral Cavity

A healthy male volunteer(s) (1-4 men) put a tablet obtained in EXAMPLES 1 to 5 and REFERENCE EXAMPLES 1 to 6 on the tongue and maintained it without any actions such as biting and nibbling, etc. The time required until the tablet completely disintegrates was measured and the mean value of the time was obtained. The results are shown in the following Table 3.

TABLE 3

| Specimen for measurement, A tablet obtained in: | Disintegration Time (Second) |
|---|---|
| EXAMPLE 1 | 17 |
| EXAMPLE 2 | 20 |
| EXAMPLE 3 | 15 |
| EXAMPLE 4 | 15 |
| EXAMPLE 5 | 17 |
| REFERENCE EXAMPLE 1 | 16 |
| REFERENCE EXAMPLE 2 | 130 |
| REFERENCE EXAMPLE 3 | 20 |
| REFERENCE EXAMPLE 4 | 50 |
| REFERENCE EXAMPLE 5 | 8 |
| REFERENCE EXAMPLE 6 | 9 |

It is clear from the results of the EXPERIMENTS 1, 2 and 3 that the present intraorally disintegrating tablets prepared in EXAMPLES 1-5 all show sufficient hardness, porosity and intraoral disintegration ability within short time. On the other hand, the tablets of REFERENCE EXAMPLES 1, 3 and 5 meet the requirements for porosity and intraoral disintegration ability though, they are not hard enough and hence inappropriate as a tablet. The tablets of REFERENCE EXAMPLE 2, which have been compressed with high compression pressure, meet the requirement for hardness though, they show low porosity and extremely poor oral disintegration ability. The tablets of REFERENCE EXAMPLE 4 have sufficient hardness and porosity; however, their taste are extremely inferior to the intraorally rapidly disintegrating tablets of the present invention, when examined by bitterness test as described in EXPERIMENT 4 below. The tablets of REFERENCE EXAMPLE 6 show sufficient hardness, porosity and intraoral disintegration ability; however, they have extremely poor drug-dissolution profile as shown in the following EXPERIMENT 5, and extremely low bioavailability as shown in the following EXPERIMENT 6.

EXPERIMENT 4

Bitterness Test

A healthy male volunteer (4 men) put an intraorally rapidly disintegrating tablet of EXAMPLE 1 or a tablet of REFERENCE EXAMPLE 4 on his tongue and maintained it without any actions such as biting and nibbling, etc., and, after disintegration, evaluated the taste according to the four-graded score as shown in Table 4. The mean score of the results is shown in Table 5.

TABLE 4

| Score | Judgement |
|---|---|
| 1 | Highly tolerable |
| 2 | Tolerable |
| 3 | Bitter-tasted but tolerable |
| 4 | Bitter-tasted and intolerable |

TABLE 5

| Tablet tested | Mean score |
|---|---|
| Rapidly disintegrating tablets of EXAMPLE 1 | 1 |
| Tablets of REFERENCE EXAMPLE 4 | 3.5 |

EXPERIMENT 5

Dissolution Test

The drug-dissolution rate in water of the intraorally rapidly disintegrating tablets prepared in EXAMPLE 1 and the tablets prepared in REFERENCE EXAMPLE 6 were evaluated according to the dissolution test Method 2 (Paddle method, Japanese Pharmacopoeia (XII revision)) under the conditions of paddle rotation of 50 rpm at 37° C. in water.

Samples were taken from dissolution fluid at 2, 5, 10, 15, 20, 25 and 30 minutes after dissolution began and subjected to measurement of absorbance at 295 nm and 450 nm. The concentration of a drug in a sample was determined using a separately prepared calibration curve showing the correlation between the absorbance and the drug concentration. The amount of a drug dissolved was calculated from the concentration of said drug and the volume of dissolution fluid.

Figure 1:
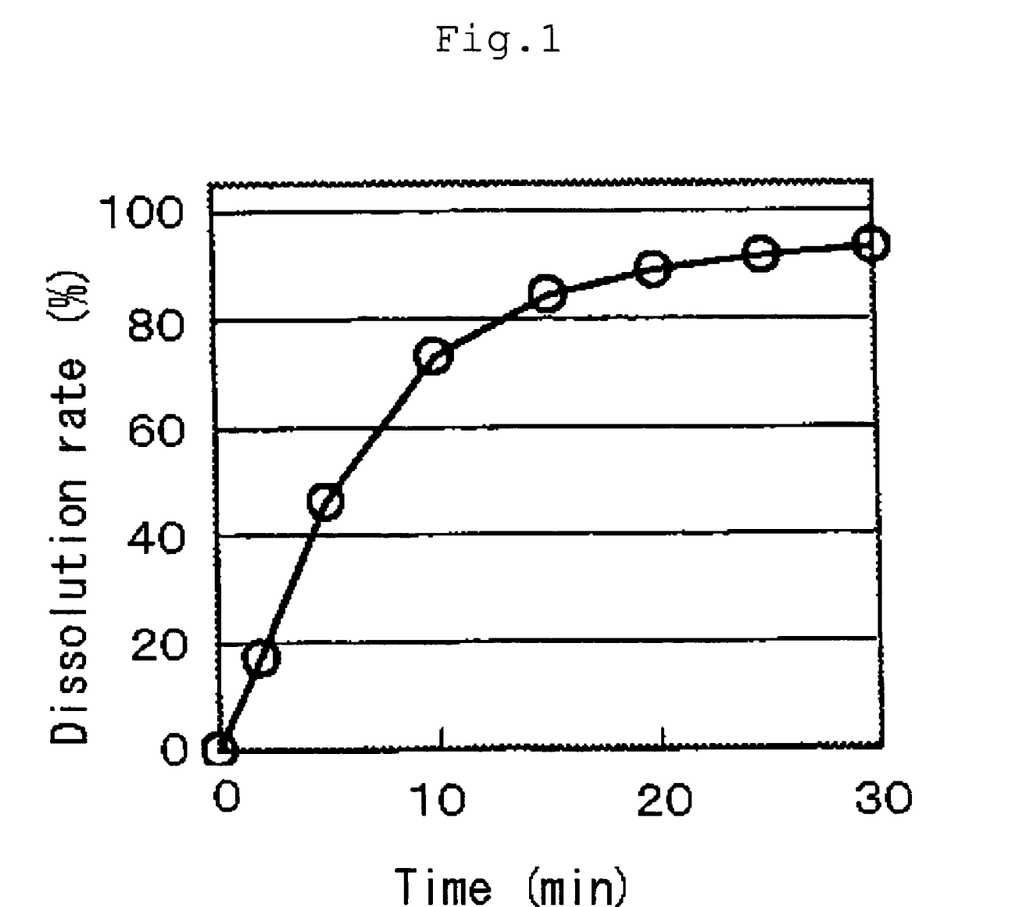
FIG. 1 is a graph showing the results of the dissolution test conducted using the intraorally rapidly disintegrating tablets of EXAMPLE 1 of the present invention.
Figure 2:
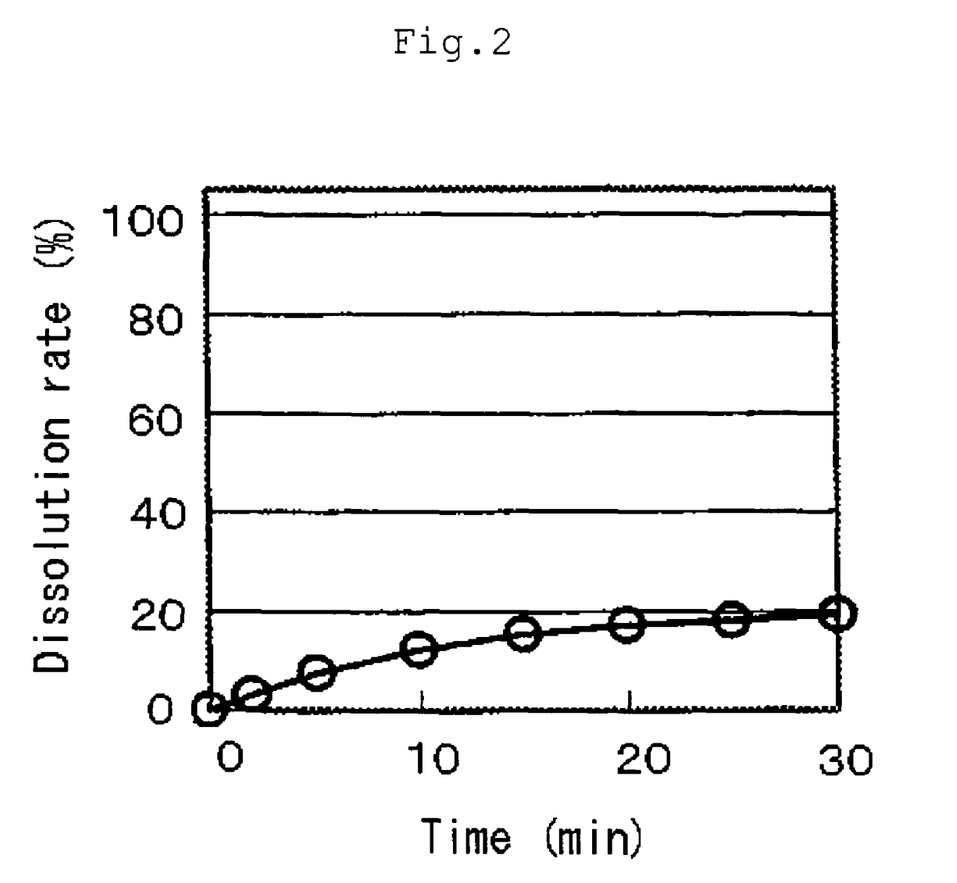
FIG. 2 is a graph showing the results of the dissolution test conducted using the tablets of the REFERENCE EXAMPLE 6.

The results are shown in FIGS. 1 and 2. As shown in FIGS. 1 and 2, the present intraorally rapidly disintegrating tablets of EXAMPLE 1 show a high dissolution rate in a short time, while the tablets of REFERENCE EXAMPLE 6 exhibit very poor dissolution profile.

EXPERIMENT 6

Measurement of Blood Concentration in Dogs

One tablet from the present intraorally rapidly disintegrating tablets of EXAMPLE 1 or that of REFERENCE EXAMPLE 6 was orally administered to male dogs starved overnight (1-2 years; 6 dogs in a group) together with water (50 mL). Blood sample (2 mL) was collected through the forearm vessel of each dog at 15, 30, 45, 60, 120, 180, 300 and 420 minutes after administration. The sample was centrifuged to separate plasma, which was then subjected to high performance liquid chromatography (HPLC). The amount of the drug in plasma was estimated on the basis of a calibration curve prepared separately using a sample containing a known concentration of drug. The blood concentration of the drug was calculated based on the thus-obtained amount of the drug and the volume of blood collected.

Figure 3:
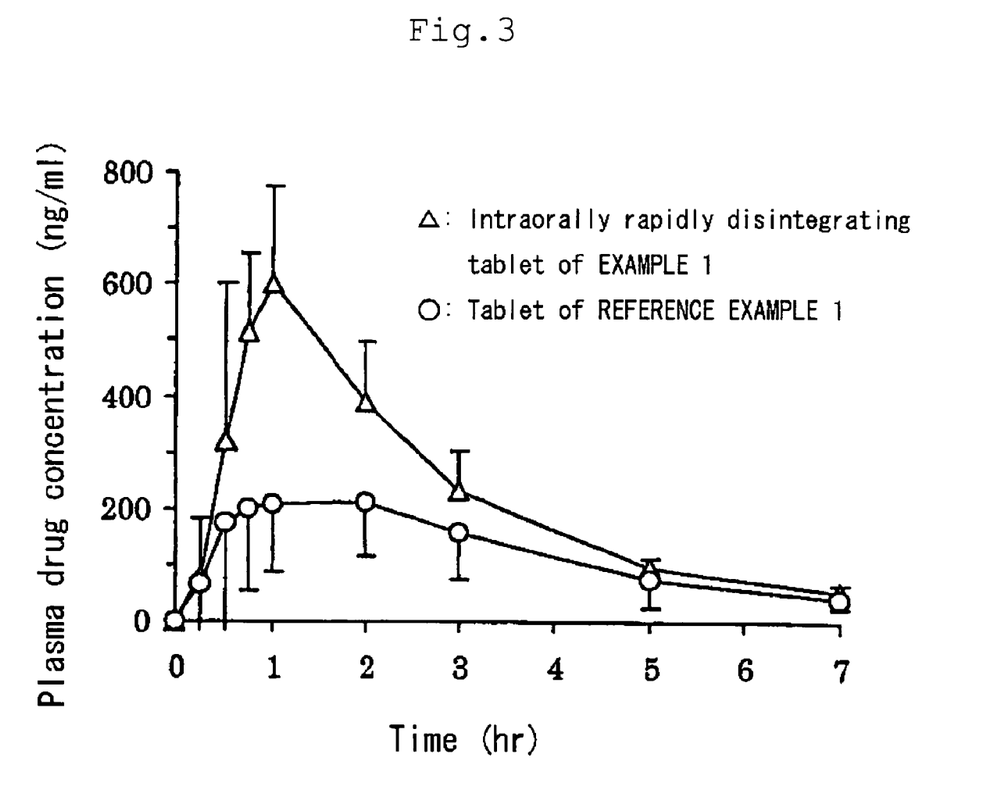
FIG. 3 is a graph showing the blood concentration of drug in dogs which received the intraorally rapidly disintegrating tablets of EXAMPLE 1 or the tablets of REFERENCE EXAMPLE 6 orally.

The results are shown in FIG. 3. As shown in FIG. 3, the present intraorally rapidly disintegrating tablet of EXAMPLE 1 presented high blood drug concentration within a short time and showed high bioavailability, while the tablet of REFERENCE EXAMPLE 6 could present only very low blood drug concentration and failed to show sufficient bioavailability.

PREPARATION 1

(1) To a solution of 4-chloro-5-ethoxycarbonyl-2-methylthiopyrimidine (25.33 g) in N,N-dimethylformamide (85 ml) are added a solution of 3-chloro-4-methoxybenzylamine (19.62 g) in N,N-dimethylformamide (15 ml) and triethylamine (16.7 ml) under ice-cooling. The mixture is stirred at. room temperature for 20 minutes, and thereto is added 3-chloro-4-methoxybenzylamine (940 mg), and the mixture is further stirred for 15 minutes. To the mixture is further added said amine (940 mg), and the mixture is stirred for 15 minutes. The reaction mixture is poured into a mixture of ice water and citric acid, and extracted with ethyl acetate. The extract is washed successively with a 10% aqueous citric acid solution, water and brine, and dried over anhydrous sodium sulfate. The solvent is evaporated in vacuo, and the residue is washed with n-hexane to give 4-(3-chloro-4-methoxybenzylamino)-5-ethoxycarbonyl-2-methylthiopyrimidine (38.34 g).

(2) To a solution of the compound (5.00 g) obtained in the above (1) in chloroform (50 ml) is added a solution of m-chloroperbenzoic acid (4.00 g) in chloroform (50 ml) under ice-cooling, and the mixture is stirred for 2 hours. The reaction mixture is washed with a saturated aqueous sodium hydrogen carbonate solution and brine, and the organic layer is dried over anhydrous sodium sulfate, and the solvent is evaporated in vacuo to give crude 4-(3-chloro-4-methoxybenzylamino)-5-ethoxycarbonyl-2-methylsulfinylpyrimidine.

(3) The crude product obtained in the above (2) is dissolved in tetrahydrofuran (40 ml), and thereto is added a solution of L-prolinol (1.50 g) and triethylamine (1.60 g) in tetrahydrofuran (10 ml) at room temperature. The mixture is stirred overnight, and the reaction mixture is diluted with ethyl acetate, and washed with aqueous sodium hydrogen carbonate solution and brine. The organic layer is dried over anhydrous sodium sulfate, and the solvent is evaporated in vacuo. The residue is purified by a column chromatography on silica gel (solvent: chloroform) and crystallized from a mixture of ether and n-hexane to give (S)-4-(3-chloro-4-methoxybenzylamino)-5-ethoxycarbonyl-2-(2-hydroxymethyl-1-pyrrolidinyl)pyrimidine (4.72 g).

(4) A mixture of the compound (3.4 g) obtained in the above (3), a 10% aqueous sodium hydroxide solution (23 ml), and dimethylsulfoxide (34 ml) is stirred at room temperature for 15 hours. The reaction mixture is poured into a 10% aqueous citric acid solution, and the precipitates are crystallized from a mixture of tetrahydrofuran and ether to give (S)-4-(3-chloro-4-methoxybenzylamino)-5-carboxy-2-(2-hydroxymethyl-1-pyrrolidinyl)pyrimidine (2.52 g).

(5) A mixture of the compound (600 mg) obtained in the above (4), 2-aminomethylpyrimidine (217 mg), 1-(3-dimethylaminopropyl)-3-ethylcarbodiimide hydrochloride (323 mg), 1-hydroxybenzotriazole monohydrate (227 mg) and N,N-dimethylformamide (12 ml) is stirred at room temperature for 8 hours, and the reaction mixture is poured into aqueous sodium hydrogen carbonate solution. The mixture is extracted with ethyl acetate, washed with brine, and dried over anhydrous sodium sulfate. The solvent is evaporated in vacuo, and the residue is purified by a column chromatography on silica gel (solvent: chloroform:methanol=50:1) to give (S)-2-(2-hydroxymethyl-1-pyrrolidinyl)-4-(3-chloro-4-methoxybenzylamino)-5-[N-(2-pyrimidylmethyl)carbamoyl]pyrimidine (610 mg).

Preparations 2-4

The corresponding starting materials are treated in the same manner as described in PREPARATION 1 to give the compounds as listed in the following Table 6.

TABLE 6

| Preparation No. | A-N— | $R^0$ | $R^1$ |
|---|---|---|---|
| 2 | imidazo-pyrazine | Cl | —NH-CH2-(2-pyrimidyl) |
| 3 | naphthyridine | Cl | —NH-CH2CH2-morpholine |
| 4 | (S)-2-hydroxymethyl-pyrrolidine (OH) | Cl | —NH-CH2-(5-pyrimidyl) |

INDUSTRIAL APPLICABILITY

According to the present intraorally rapidly disintegrating tablet, which contains a medicinal substance being hardly water-soluble under neutral or alkaline conditions and being highly water-soluble under acidic conditions yet presenting unpleasant taste under acidic conditions, the dissolution profile of the medicinal substance is increased by compounding a water-soluble acidic substance thereby achieving the rapid disintegration and improving bioavailability; and the initial contact of a medicinal substance with an acidic substance is avoided by coating at least one of the medicinal and water-soluble acidic substances with a water-soluble coating agent being insoluble in an alcoholic solvent and thereby preventing expression of unpleasant taste in the oral cavity. Furthermore, according to the present invention, a mixture which is compounded with a water-soluble binding agent being soluble in alcoholic solvent and a water-soluble saccharide has been subjected to tableting under a low pressure and then treatment with an alcoholic solvent, whereby the resultant intraorally rapidly disintegrating tablets meet the requirements for hardness and porosity, show rapid disintegration in the oral cavity, a high drug-dissolution rate, good bioavailability and early onset of efficacy. Accordingly, the present invention is especially preferably applicable to a medicinal substance which is expected to exhibit its efficacy shortly after ingestion, for example, within 1 hour, such as substances having a cGMP-specific phosphodiesterase inhibitory activity.

The invention claimed is:

1. An intraorally rapidly disintegrating tablet having hardness of 20 N or more and porosity within the range of 25% to 50%, comprising the following ingredients:
    i) a medicinal substance selected from the group consisting of:
        (S)-2-(2-hydroxymethyl-1-pyrrolidinyl)-4-(3-chloro-4-methoxybenzylamino)-5[N-(2-pyrimidinylmethyl)-carbamoyl]pyrimidine;
        2-(5,6,7,8-tetrahydroimidazo[1,2-a]pyrazin-7-yl)-4-(3-chloro-4-methoxybenzylamino)-5-[N-(2-pyrimidinylmethyl)-carbamoyl]pyrimidine;
        2-(5,6,7,8-tetrahydro-1,7-naphthyridin-7-yl)-4-(3-chloro-4-methoxybenzylamino)-5-[N-(2-morpholinoethyl)carbamoyl]-pyrimidine; and
        (S)-2-(2-hydroxymethyl-1-pyrrolidinyl)-4-(3-chloro-4-methoxybenzylamino)-5-[N-(5-pyrimidinylmethyl)carbamoyl]-pyrimidine;
    ii) a water-soluble acidic substance selected from the group consisting of fumaric acid, tartaric acid, succinic acid, malic acid, ascorbic acid and aspartic acid;
    iii) a water-soluble binding agent being soluble in alcoholic solvent selected from the group consisting of polyvinylpyrrolidone and hydroxypropylcellulose; and
    iv) a water-soluble saccharide selected from the group consisting of mannitol, xylitol, erythritol, maltitol, sorbitol and lactose,
    wherein at least one of the ingredients (i) and (ii) is coated with a water-soluble coating agent being insoluble in an alcoholic solvent selected from the group consisting of hydroxypropylmethyl cellulose, methyl cellulose, hydroxyethyl cellulose, dextran, pullulan, agar, sodium arginate, polyvinyl alcohol and gelatine, and which tablet is obtainable by subjecting a mixture containing the ingredients (i), (ii), (iii) and (iv) and optionally one or more pharmaceutically acceptable additives for pharmaceutical preparations to compression, treating the compressed products with an alcohol, and removing the alcohol.

2. The intraorally rapidly disintegrating tablet according to claim 1, of which disintegration time in the oral cavity is within 60 seconds.

3. The intraorally rapidly disintegrating tablet according to claim 1, wherein only the water-soluble acidic substance is coated with a water-soluble coating agent being insoluble in alcoholic solvent.

4. The intraorally rapidly disintegrating tablet according to claim 1, which comprises 1-70 w/w % of a medicinal substance, 0.1-50 w/w % of a water-soluble acidic substance, 0.02-10 w/w % of a water-soluble coating agent, 0.1-30 w/w % of a water-soluble binding agent, and 5-95 w/w % of a water-soluble saccharide.

5. The intraorally rapidly disintegrating tablet according to claim 1, which further contains one or more pharmaceutically acceptable additives for pharmaceutical preparations.

6. The intraorally rapidly disintegrating tablet according to claim 5, wherein the pharmaceutically acceptable additive for pharmaceutical preparations is (1) a lubricant selected from the group consisting of magnesium stearate, calcium stearate, talc, light anhydrous silicic acid and anhydrous silica dioxide and/or (2) a sweetening agent selected from the group consisting of saccharine, aspartame and Stevia.

7. A process for preparing an intraorally rapidly disintegrating tablet having hardness of 20 N or more and porosity within the range of 25% to 50%, comprising the following steps (A)-(C):
    (A) preparing a mixture comprising:
        (i) a medicinal substance selected from the group consisting of:
            (S)-2-(2-hydroxymethyl-1-pyrrolidinyl)-4-(3-chloro-4-methoxybenzylamino)-5-[N-(2-pyrimidinylmethyl)-carbamoyl]pyrimidine;
            2-(5,6,7,8-tetrahydroimidazo[1,2-a]pyrazin-7-yl)-4-(3-chloro-4-methoxybenzylamino)-5-[N-(2-pyrimidinylmethyl)-carbamoyl]pyrimidine;
            2-(5,6,7,8-tetrahydro-1,7-naphthyridin-7-yl)-4-(3-chloro-4-methoxybenzylamino)-5[N-(2-morpholinoethyl)carbamoyl]-pyrimidine; and
            (S)-2-(2-hydroxymethyl-1-pyrrolidinyl)-4-(3-chloro-4-methoxybenzylamino)-5-[N-(5-pyrimidinylmethyl)carbamoyl]-pyrimidine;
        ii) a water-soluble acidic substance selected from the group consisting of fumaric acid, tartaric acid, succinic acid, malic acid, ascorbic acid and aspartic acid;
        iii) a water-soluble binding agent being soluble in alcoholic solvent selected from the group consisting of polyvinylpyrrolidone and hydroxypropylcellulose; and
        iv) a water-soluble saccharide selected from the group consisting of mannitol, xylitol, erythritol, maltitol, sorbitol and lactose,
        wherein at least one of the ingredients (i) and (ii) is coated with a water-soluble coating agent being insoluble in alcoholic solvent selected from the group consisting of hydroxypropylmethyl cellulose, methyl cellulose, hydroxyethyl cellulose, dextran, pullulan, agar, sodium arginate, polyvinyl alcohol and gelatine,
    (B) subjecting the mixture obtained in the step (A) above to compression under a low compressing pressure, and
    (C) treating the tablets obtained in the compression in step (B) with an alcohol followed by drying.

8. The process according to claim 7, wherein the compression in step (B) is carried out under a compressing pressure of 5 to 30 MPa.

9. The process according to claim 8, wherein the compression in step (B) is carried out by any one of following methods:
    (b-1) a method wherein tableting is conducted using a mixture containing a lubricant and a fluidizing agent and a mixture of step (A) by turns;
    (b-2) a method wherein tableting is conducted while spraying a lubricant powder, and
    (b-3) a method wherein compression is conducted through a polymer film.

10. The process according to claim 7, wherein the alcoholic solvent is ethanol.

11. The intraorally rapidly disintegrating tablet according to claim 1, wherein the alcoholic solvent is ethanol.

12. An intraorally rapidly disintegrating tablet having hardness of 20 N or more and porosity within the range of 25% to 50%, which is obtainable by a process comprising the following steps (A)-(C):

(A) preparing a mixture comprising:
 (i) a medicinal substance selected from the group consisting of
  (S)-2-(2-hydroxymethyl-1-pyrrolidinyl)-4-(3-chloro-4-methoxybenzylamino)-5-[N-(2-pyrimidinylmethyl)-carbamoyl]pyrimidine;
  2-(5,6,7,8-tetrahydroimidazo[1,2-a]pyrazin-7-yl)-4-(3-chloro-4-methoxybenzylamino)-5-[N-(2-pyrimidinylmethyl)-carbamoyl]-pyrimidine;
  2-(5,6,7,8-tetrahydro-1,7-naphthyridin-7yl)-4-(3-chloro-4-methoxybenzylamino)-5[N-(2-morpholinoethyl)carbamoyl]-pyrimidine; and
  (S)-2-(2-hydroxymethyl-1-pyrrolidinyl)-4-(3-chloro-4-methoxybenzylamino)-5[N-(5-pyrimidinylmethyl) carbamoyl]-pyrimidine;
 ii) a water-soluble acidic substance selected from the group consisting of fumaric acid, tartaric acid, succinic acid, malic acid, ascorbic acid and aspartic acid;
 iii) a water-soluble binding agent being soluble in alcoholic solvent selected from the group consisting of polyvinylpyrrolidone and hydroxypropylcellulose; and
 iv) a water-soluble saccharide selected from the group consisting of mannitol, xylitol, erythritol, maltitol, sorbitol and lactose,
 by admixing the uncoated ingredient (i) with the ingredient (iv), granulating the mixture while adding an aqueous solution of the ingredient (iii), drying the resultant granules and mixing the granules with the ingredient (ii) coated with a water-soluble coating agent being insoluble in an alcoholic solvent; or
 by admixing the uncoated ingredient (ii) with the ingredient (iv), granulating the mixture while adding an aqueous solution of the ingredient (iii), drying the resultant granules and mixing the granules with the ingredient (i) coated with a water-soluble coating agent being insoluble in an alcoholic solvent; or
 by granulating the ingredient (iv) while adding an aqueous solution of the ingredient (iii), drying the resultant granules and mixing the granules with the ingredient (i) coated with a water-soluble coating agent and the ingredient (ii) coated with a water-soluble coating agent, (B) subjecting the mixture obtained in the above step (A), optionally after admixing with one or more additives, to compression under a low compression pressure, and (C) treating the tablets obtained in the compression in step (B) with an alcohol followed by drying.

* * * * *